(12) United States Patent
Izumi et al.

(10) Patent No.: US 9,080,996 B2
(45) Date of Patent: Jul. 14, 2015

(54) SAMPLE ANALYZER AND METHOD FOR CONTROLLING A SAMPLE ANALYZER

(71) Applicants: Sysmex Corporation, Kobe-shi, Hyogo (JP); Arkray, Inc., Kyoto-shi, Kyoto (JP)

(72) Inventors: Takayoshi Izumi, Hyogo (JP); Keisuke Tsutsumida, Hyogo (JP); Toru Mizumoto, Hyogo (JP); Shinya Nakajima, Kyoto (JP); Koji Fujimoto, Kyoto (JP)

(73) Assignees: SYSMEX CORPORATION, Hyogo (JP); ARKRAY, INC., Kyoto (JP)

( * ) Notice: Subject to any disclaimer, the term of this patent is extended or adjusted under 35 U.S.C. 154(b) by 308 days.

(21) Appl. No.: 13/629,045

(22) Filed: Sep. 27, 2012

(65) Prior Publication Data
US 2013/0019698 A1 Jan. 24, 2013

Related U.S. Application Data

(63) Continuation of application No. PCT/JP2011/057764, filed on Mar. 29, 2011.

(30) Foreign Application Priority Data

Mar. 30, 2010 (JP) .................................. 2010-076525

(51) Int. Cl.
*G01N 35/02* (2006.01)
*G01N 33/493* (2006.01)
(Continued)

(52) U.S. Cl.
CPC .......... *G01N 35/0092* (2013.01); *G01N 33/493* (2013.01); *G01N 2035/0415* (2013.01)

(58) Field of Classification Search
CPC ............ G01N 33/493; G01N 35/0092; G01N 2035/0415
USPC ............ 73/61.59, 61.63, 61.68, 61.71, 64.56, 73/863.01, 864.91; 422/65, 67, 105, 422/107–108, 119; 436/47, 50, 180; 700/228, 230
See application file for complete search history.

(56) References Cited

U.S. PATENT DOCUMENTS 8,062,591 B2 * 11/2011 Yamamoto .................. 422/65 X
8,329,102 B2 * 12/2012 Koike ............................. 422/65
(Continued)

FOREIGN PATENT DOCUMENTS

CN 101526540 A 9/2009
EP 2237033 A1 * 10/2010 ........... G01N 33/493
(Continued)

OTHER PUBLICATIONS

International Preliminary Report on Patentability for International Application No. PCT/JP2011/057764, dated Nov. 13, 2012, 6 pages.
(Continued)

*Primary Examiner* — Thomas P Noland
(74) *Attorney, Agent, or Firm* — Brinks Gilson & Lione

(57) ABSTRACT

A sample analyzer which transports and analyzes samples, includes: a first measurement apparatus which measures samples; a second measurement apparatus which is arranged downstream, in a transport direction, from the first measurement apparatus, and which measures samples; a transporting apparatus which transports samples to a first supply position for supplying a sample to the first measurement apparatus, and to a second supply position for supplying a sample to the second measurement apparatus; and a controller which controls transportation of a sample present at the first supply position, in accordance with a processing status of a sample present at the second supply position.

16 Claims, 8 Drawing Sheets

(51) Int. Cl.
*G01N 35/04* (2006.01)
*G01N 35/00* (2006.01)

(56) References Cited

U.S. PATENT DOCUMENTS

| | | | |
|---|---|---|---|
| 8,347,743 B2 * | 1/2013 | Hamada et al. | .... G01N 35/0092 |
| 8,455,256 B2 * | 6/2013 | Yamato et al. | ................ 436/47 |
| 8,534,456 B2 * | 9/2013 | Kimura et al. | . G01N 2035/0415 |
| 8,641,988 B2 * | 2/2014 | Mizumoto et al. | .......... 422/65 X |
| 8,865,072 B2 * | 10/2014 | Nagai et al. | .................... 422/67 |
| 2009/0223308 A1 | 9/2009 | Fukuma | |
| 2009/0223311 A1 | 9/2009 | Hamada et al. | |
| 2010/0248292 A1 * | 9/2010 | Kuwano et al. | .... G01N 35/0092 |
| 2010/0248293 A1 * | 9/2010 | Kuwano et al. | ........ G01N 35/02 |
| 2011/0022327 A1 * | 1/2011 | Busenhart et al. | ............. 702/19 |
| 2011/0076194 A1 * | 3/2011 | Kitagawa et al. | ............... 422/65 |
| 2011/0076780 A1 * | 3/2011 | Yamato et al. | ............. 422/65 X |
| 2013/0079919 A1 * | 3/2013 | Fukuma et al. | ............. 422/67 X |

FOREIGN PATENT DOCUMENTS

| | | | | |
|---|---|---|---|---|
| EP | 2299282 A2 * | 3/2011 | ............ | G01N 35/04 |
| JP | 58144753 A * | 8/1983 | .................... | 422/65 |
| JP | 59170771 A * | 9/1984 | .................... | 436/47 |
| JP | 03-279863 A | 12/1991 | | |
| JP | 06-102272 A | 4/1994 | | |
| JP | 06138120 A * | 5/1994 | .......... | G01N 33/493 |
| JP | 07049346 A * | 2/1995 | .......... | G01N 33/493 |
| JP | 09243645 A * | 9/1997 | ............ | G01N 35/04 |
| JP | 09-274044 A | 10/1997 | | |
| JP | 09-329597 A | 12/1997 | | |
| JP | 10-300756 A | 11/1998 | | |
| JP | 2009-216442 A | 9/2009 | | |
| JP | 2009-229232 A | 10/2009 | | |

OTHER PUBLICATIONS

Office Action, and English language translation thereof, in corresponding Chinese Application No. 201180015960.X, dated Oct. 18, 2013, 11 pages.

International Search Report for International Application No. PCT/JP2011/057764, dated Jun. 14, 2011, 2 pages.

* cited by examiner

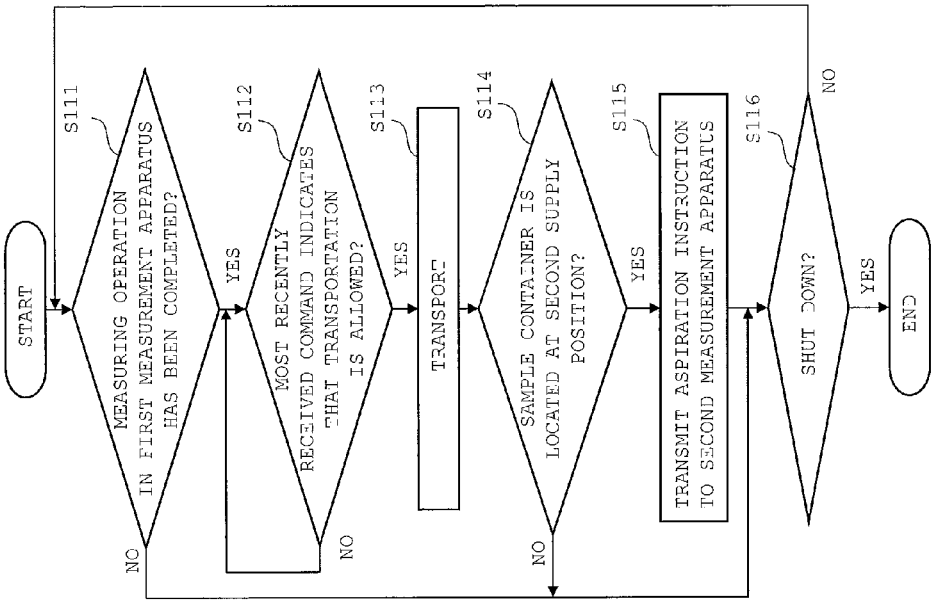
FIG. 5A  MEASUREMENT PROCESS PERFORMED BY FIRST MEASUREMENT APPARATUS
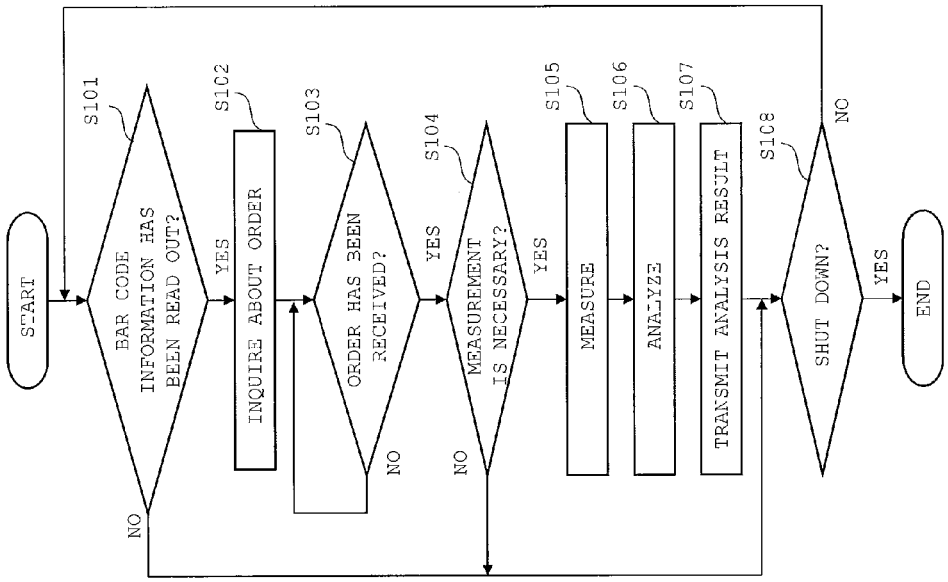
FIG. 5B  TRANSPORT PROCESS PERFORMED BY FIRST MEASUREMENT APPARATUS

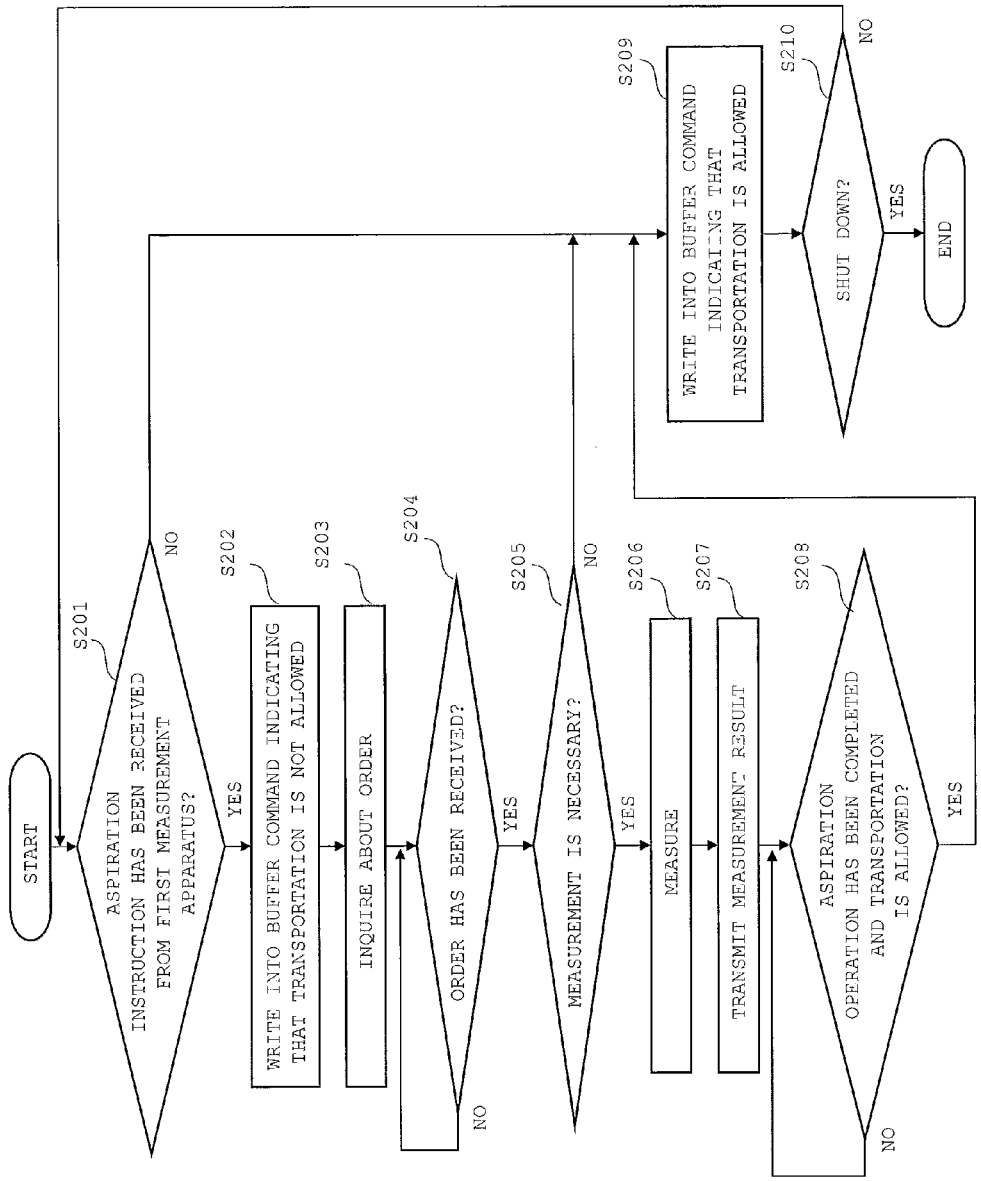

ORDER PROCESS PERFORMED BY
INFORMATION PROCESSING APPARATUS

COMMAND TRANSMITTING PROCESS PERFORMED
BY SECOND MEASUREMENT APPARATUS

SAMPLE ANALYZER AND METHOD FOR CONTROLLING A SAMPLE ANALYZER

RELATED APPLICATIONS

This application is a continuation of PCT/JP2011/057764 filed on Mar. 29, 2011, which claims priority to Japanese Application No. 2010-076525 filed on Mar. 30, 2010. The entire contents of these applications are incorporated herein by reference.

BACKGROUND OF THE INVENTION

1. Field of the Invention

The present invention relates to sample analyzers which perform predetermined processes such as tests and analyses onto samples such as urine and blood.

2. Description of Related Art

Sample analysis systems which each include a plurality of analyzers and a transporting apparatus which transports samples to the plurality of analyzers are known.

As such a sample analysis system, for example, Patent Literature 1 (Japanese Laid-Open Patent Publication No. H9-329597) discloses a urinary sediment testing system which includes a semi-quantitative analyzer, a urinary sediment analyzer, a quantitative analyzer, and a transport line which transports urine samples to them. Each analyzer is provided with a dedicated transport mechanism which receives a sample rack from the transport line and returns the received sample rack to the transport line again via a sampling position. Moreover, the transport mechanism is provided with regions for retaining sample racks on the sending-in side and the sending-out side, respectively.

Further, Patent Literature 2 (Japanese Laid-Open Patent Publication No. 2009-229232) discloses an analysis system which includes two analyzers, two transport mechanisms arranged in front of the respective analyzers, and a connection member connecting the two transport mechanisms. In this analysis system, a region for retaining sample racks is provided on the side of the connection member connecting the two transport mechanisms.

In the urinary sediment testing system described in Patent Literature 1, since regions for retaining sample racks are provided on the sending-in side and the sending-out side of each of the transport mechanisms, the system is large. In the analysis system described in Patent Literature 2, since the region for retaining sample racks is provided on the side of the connection member connecting the two transport mechanisms, the system is large, as in the case of Patent Literature 1.

SUMMARY OF THE INVENTION

A sample analyzer according to a main aspect of the present invention is a sample analyzer which transports and analyzes samples, including: a first measurement apparatus which measures samples; a second measurement apparatus which is arranged downstream, in a transport direction, from the first measurement apparatus, and which measures samples; a transporting apparatus which transports samples to a first supply position for supplying a sample to the first measurement apparatus, and to a second supply position for supplying a sample to the second measurement apparatus; and a controller which controls transportation of a sample present at the first supply position, in accordance with a processing status of a sample present at the second supply position.

In the sample analyzer according to the present aspect, the sample present at the first supply position is transported, in accordance with the processing status of the sample present at the second supply position. Thus, the sample present at the second supply position is not transported unintentionally. This eliminates the necessity of providing a region for retaining samples, between the first supply position and the second supply position, and thus, the sample analyzer can be downsized.

BRIEF DESCRIPTION OF THE DRAWINGS

These and other objects, and novel features of the present invention will become more apparent upon reading the following detailed description of the embodiment along with the accompanying drawings.

FIGS. 5A and 5B show flow charts respectively showing a measurement process and a transport process performed by the first measurement apparatus according to an embodiment;

FIG. 6 is a flow chart showing a measurement process performed by the second measurement apparatus according to an embodiment;

It should be noted that the drawings are solely for description and do not limit the scope of the present invention by any degree.

The drawings are provided mainly for describing the present invention, and do not limit the scope of the present invention.

DETAILED DESCRIPTION OF THE PREFERRED EMBODIMENTS

The present embodiment is realized by applying the present invention to a clinical sample analyzer which performs tests (urine qualitative tests) regarding urine protein, urine sugar, and the like, and tests (urinary sediment tests) regarding red blood cells, white blood cells, epithelial cells, and the like contained in urine. A urinary sediment test is performed on a sample for which it has been determined that a urinary sediment test is necessary as a result of a urine qualitative test performed on the sample. In the present embodiment, a plurality of sample containers respectively containing different samples are set in a rack, the rack is set in a sample analyzer, and testing of the samples are performed.

Hereinafter, a sample analyzer according to the present embodiment will be described with reference to the drawings.

Figure 1:
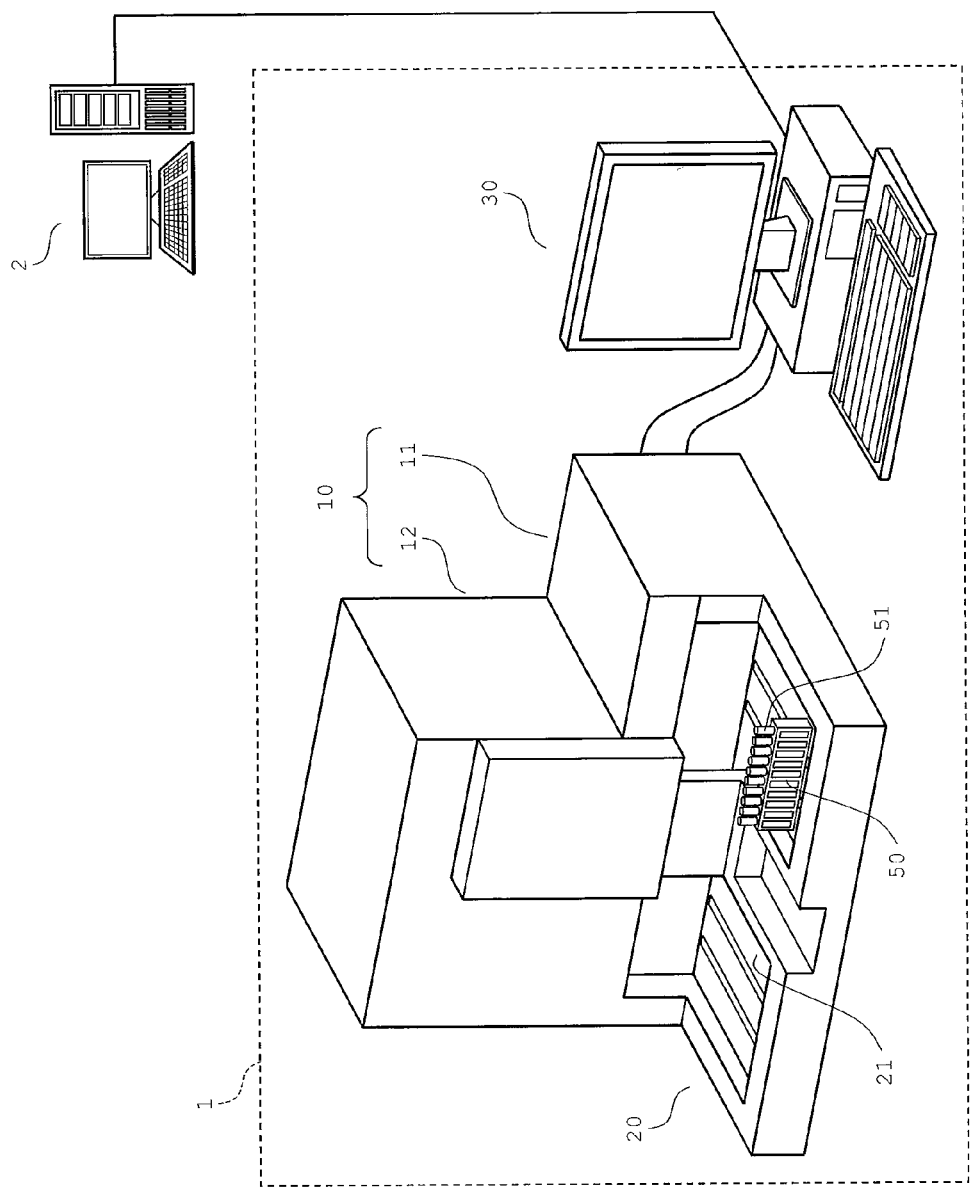
FIG. 1 shows an overall configuration of a system including a sample analyzer according to an embodiment.

FIG. 1 shows an overall configuration of a system including a sample analyzer 1. The sample analyzer 1 according to the present embodiment includes a sample measurement apparatus 10, a transporting apparatus 20, and an information processing apparatus 30.

The sample measurement apparatus 10 includes a first measurement apparatus 11 which performs urine qualitative tests and a second measurement apparatus 12 which performs urinary sediment tests. The first measurement apparatus 11 and the second measurement apparatus 12 are communicably connected to each other. Moreover, the first measurement apparatus 11 and the second measurement apparatus 12 are each communicably connected to the information processing apparatus 30. Further, the first measurement apparatus 11 is communicably connected to the transporting apparatus 20.

The transporting apparatus 20 is a single unit common for the first measurement apparatus 11 and the second measurement apparatus 12. The transporting apparatus 20 is mounted to the front face of the sample measurement apparatus 10 and includes a transport path 21. The transport path 21 has a bottom face of a flat plate shape, provided at a lower level than the upper face of the transporting apparatus 20. In a sample rack 50 which is transported on the transport path 21, ten holders are formed so as to be able to hold ten sample containers 51, respectively. By being held in a holder of the sample rack 50, each sample container 51 is transported on the transport path 21, along with the sample rack 50. A bar code label (not shown) for identifying a sample is affixed to a lateral side of the sample container 51. The information processing apparatus 30 is communicably connected to a host computer 2 via a communication line.

Figure 2:
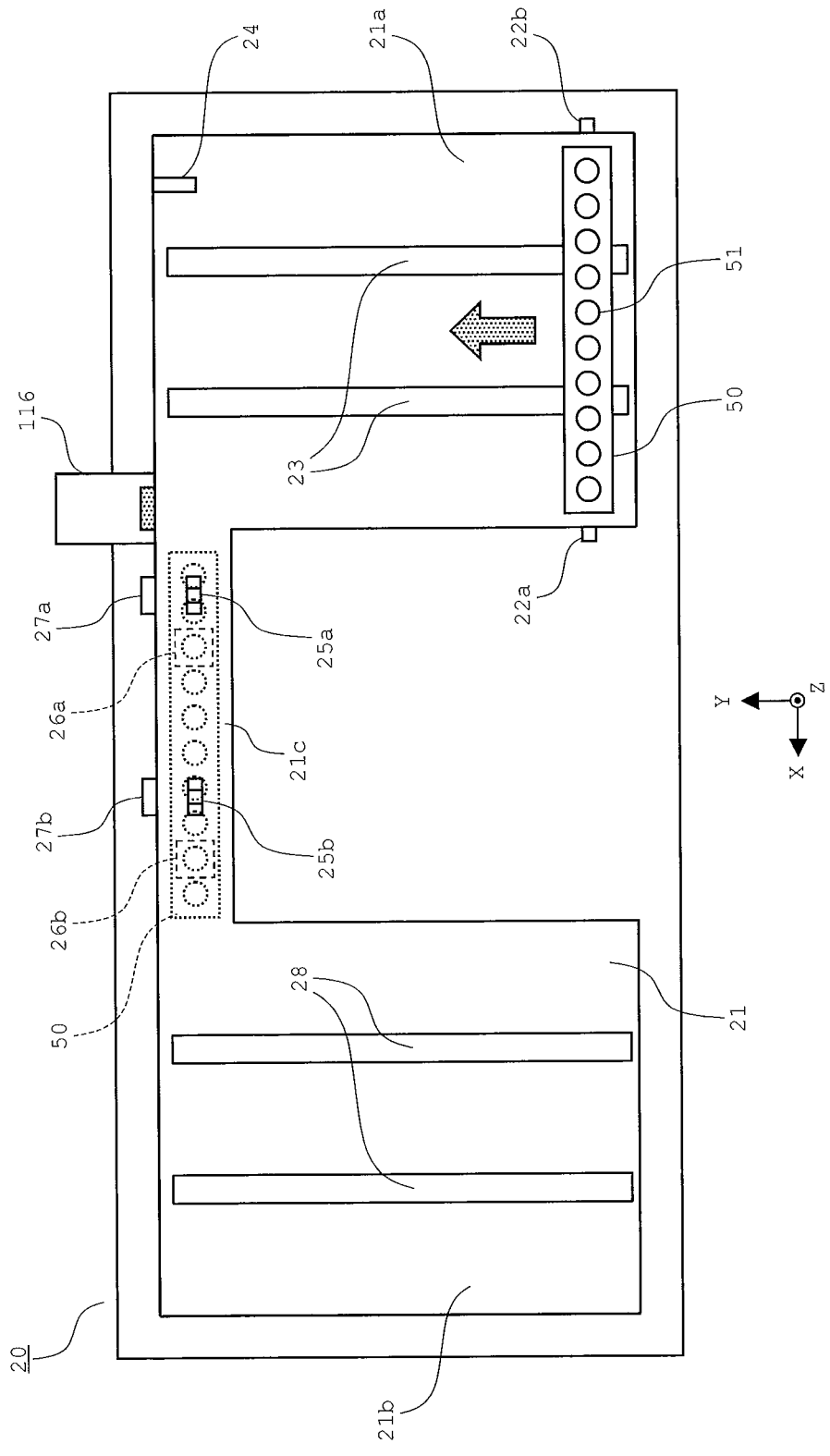
FIG. 2 is a plan view showing a configuration of a transporting apparatus according to an embodiment, viewed from above.

FIG. 2 is a plan view showing a configuration of the transporting apparatus 20, viewed from above.

The transporting apparatus 20 includes the transport path 21, transmissive sensors 22a and 22b, belts 23 and 28, a pushing-out mechanism 24, lateral transportation sensors 25a and 25b, and reflective sensors 27a and 27b. The transport path 21 includes a right vessel region 21a, a left vessel region 21b, and a connection region 21c. The right vessel region 21a and the left vessel region 21b are connected to each other by means of the connection region 21c.

The transmissive sensors 22a and 22b are composed of a light emitter and a light receiver, and detect a sample rack 50 located at the front side in the right vessel region 21a (at the end in the Y-axis negative direction). Based on an output signal from the sensors 22a and 22b, it is detected that a sample rack 50 is placed at the front side in the right vessel region 21a by a user. The belt 23 is provided in the right vessel region 21a, and moves the sample rack 50 placed in the right vessel region 21a in the Y-axis positive direction, to locate it to the rear side in the right vessel region 21a (at the end in the Y-axis positive direction).

The pushing-out mechanism 24 includes a driving section (not shown) further to the rear than the transport path 21, and is configured such that a pushing-out claw moves from the right rear of the right vessel region 21a to the left rear of the left vessel region 21b in the left-right direction (X-axis direction). In FIG. 2, only the claw of the pushing-out mechanism 24 is shown. By the pushing-out mechanism 24 pushing the right-end side face of the sample rack 50, the sample rack 50 located at the rear side of the right vessel region 21a is moved, via the connection region 21c, to the rear side of the left vessel region 21b. As will be described later, a process of transporting the sample rack 50 near the connection region 21c is performed as appropriate, in accordance with measuring operation statuses of the first measurement apparatus 11 and the second measurement apparatus 12.

A bar code reader 116 reads out bar code information from a bar code label affixed to the sample container 51 located in front of (Y-axis negative direction) the bar code reader 116. It should be noted that the bar code reader 116 is controlled by a controller of the first measurement apparatus 11, as described later.

Each of the lateral transportation sensors 25a and 25b has a claw slightly projecting upward (Z-axis positive direction) from the bottom face of the transport path 21 (the connection region 21c). When the sample rack 50 is moved from right to left (X-axis positive direction), the states of the claws of the lateral transportation sensors 25a and 25b change between a projecting state and a non-projecting state relative to the bottom face of the transport path 21, in accordance with opening parts and non-opening parts which are formed in the bottom face of the sample rack 50 at intervals between accommodation parts for the sample container 51. Accordingly, it is determined as appropriate whether the distance by which the pushing-out mechanism 24 has been moved agrees with the distance by which the sample rack 50 has been moved.

A first supply position 26a and a second supply position 26b are positions at which samples contained in sample containers 51 are aspirated by the first measurement apparatus 11 and the second measurement apparatus 12, respectively. For example, as shown by the broken line in FIG. 2, a sample rack 50 is located in the connection region 21c. The interval between the first supply position 26a and the second supply position 26b is set to be shorter than the interval between the holder at the left end (at the end in the X-axis positive direction in FIG. 2) of the sample rack 50 and the holder at the right end (at the end in the X-axis negative direction in FIG. 2) thereof. Moreover, the interval between the first supply position 26a and the second supply position 26b is set such that two holders of one sample rack 50 are concurrently located at the first supply position 26a and the second supply position 26b, respectively.

When measurement is performed by the first measurement apparatus 11, a nozzle (not shown) provided in the first measurement apparatus 11 is inserted into the sample container 51 located at the first supply position 26a. Subsequently, the sample contained in the sample container 51 is aspirated by the nozzle. The aspirated sample is measured in the first measurement apparatus 11. When the aspiration is completed, the nozzle is drawn from the sample container 51, and the sample rack 50 holding this sample container 51 is moved leftward by the pushing-out mechanism 24.

Also when measurement is performed by the second measurement apparatus 12, a nozzle (not shown) provided in the second measurement apparatus 12 is similarly inserted into the sample container 51 located at the second supply position 26b. Subsequently, the sample contained in the sample container 51 is aspirated by the nozzle. The aspirated sample is measured in the second measurement apparatus 12. When the aspiration is completed, the nozzle is drawn from the sample container 51, and the sample rack 50 holding this sample container 51 is moved leftward by the pushing-out mechanism 24.

The reflective sensors 27a and 27b detect whether holders for holding sample containers 51 of the sample rack 50 located in front of (Y-axis negative direction) the reflective sensors 27a and 27b are holding sample containers 51, respectively. Accordingly, it is possible to confirm again whether the sample container 51 whose bar code information was read by the bar code reader 116 is being held in a corresponding holder of the sample rack 50, before aspiration therefor is performed.

The belt 28 is provided in the left vessel region 21b, and moves the sample rack 50 located at the rear side (at the end in the Y-axis positive direction) of the left vessel region 21b, in the Y-axis negative direction, thereby locating it at the front (at the end in the Y-axis negative direction) of the left vessel region 21b. Then, the sample rack 50 located at the front of the left vessel region 21b is taken out by the user.

Figure 3:
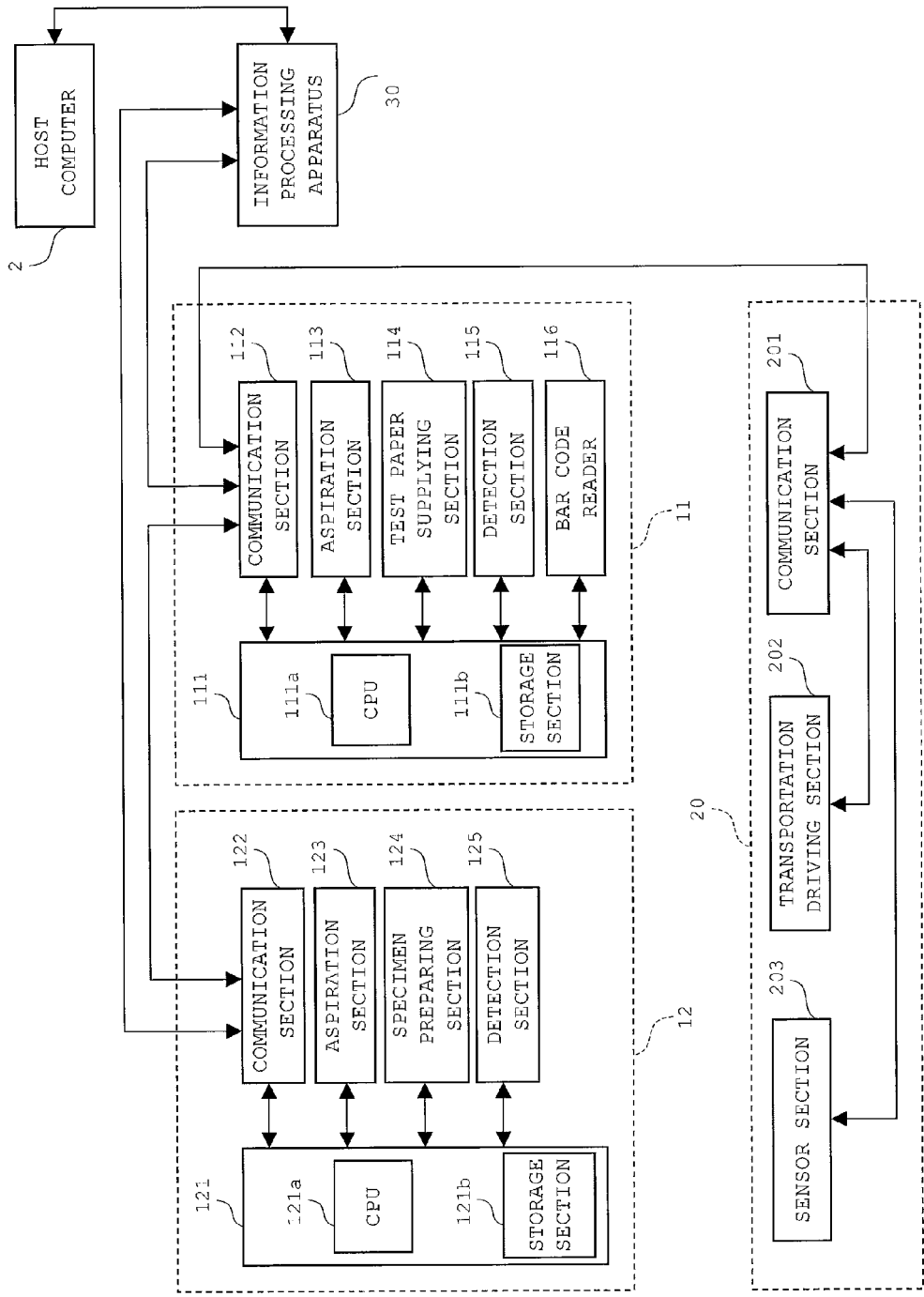
FIG. 3 shows circuit configurations of a first measurement apparatus, a second measurement apparatus, and a transporting apparatus according to an embodiment.

FIG. 3 shows circuit configurations of the first measurement apparatus 11, the second measurement apparatus 12, and the transporting apparatus 20.

The first measurement apparatus 11 includes a controller 111, a communication section 112, an aspiration section 113, a test paper supplying section 114, a detection section 115, and the bar code reader 116. The controller 111 includes a CPU 111a and a storage section 111b. The CPU 111a executes computer programs stored in the storage section 111b and controls sections of the first measurement apparatus 11. Moreover, the CPU 111a controls sections of the transporting apparatus 20 via the communication section 112. The storage section 111b includes storage means such as a ROM, a RAM, and a hard disk.

The communication section 112 processes signals from the controller 111 to output the resultant signals to the second measurement apparatus 12, the transporting apparatus 20, and the information processing apparatus 30, and processes signals from the second measurement apparatus 12, the transporting apparatus 20, and the information processing apparatus 30 to output the resultant signals to the controller 111. The aspiration section 113 aspirates the sample in the sample container 51 located at the first supply position 26a via the nozzle of the first measurement apparatus 11. The test paper supplying section 114 takes out test paper necessary for measurement from a test paper feeder in which test paper is stored, and applies as a spot the sample aspirated by the aspiration section 113 onto the taken-out test paper. The detection section 115 measures the test paper on which the sample has been applied as a spot. A measurement result obtained by the measurement is outputted to the controller 111 and analyzed by the controller 111. The bar code reader 116 reads out bar code information from the bar code label affixed to the sample container 51, and outputs the bar code information to the controller 111.

The second measurement apparatus 12 includes a controller 121, a communication section 122, an aspiration section 123, a specimen preparing section 124, and a detection section 125. The controller 121 includes a CPU 121a and a storage section 121b. The CPU 121a executes computer programs stored in the storage section 121b and controls sections of the second measurement apparatus 12. The storage section 121b includes storage means such as a ROM, a RAM, and a hard disk.

The communication section 122 processes signals from the controller 121 to output the resultant signals to the first measurement apparatus 11 and the information processing apparatus 30, and processes signals from the first measurement apparatus 11 and the information processing apparatus 30 to output the resultant signals to the controller 121. The aspiration section 123 aspirates the sample in the sample container 51 located at the second supply position 26b via the nozzle of the second measurement apparatus 12. The specimen preparing section 124 mixes and stirs the sample aspirated by the aspiration section 123 and a reagent necessary for measurement, to prepare a specimen for measurement to be performed by the detection section 125. The detection section 125 measures the specimen prepared by the specimen preparing section 124. A measurement result obtained by the measurement is outputted to the controller 121.

The transporting apparatus 20 includes a communication section 201, a transportation driving section 202, and a sensor section 203. The communication section 201 processes signals from the first measurement apparatus 11 to output the resultant signals to sections of the transporting apparatus 20, and processes signals from sections of the transporting apparatus 20 to output the resultant signals to the first measurement apparatus 11.

The transportation driving section 202 is controlled by the CPU 111a of the first measurement apparatus 11. It should be noted that the transportation driving section 202 includes the belts 23 and 28 and the pushing-out mechanism 24 shown in FIG. 2. The sensor section 203 outputs output signals from various sensors, to the first measurement apparatus 11 via the communication section 201. It should be noted that the sensor section 203 includes the sensors 22a and 22b, the lateral transportation sensors 25a and 25b, and the sensors 27a and 27b shown in FIG. 2.

Figure 4:
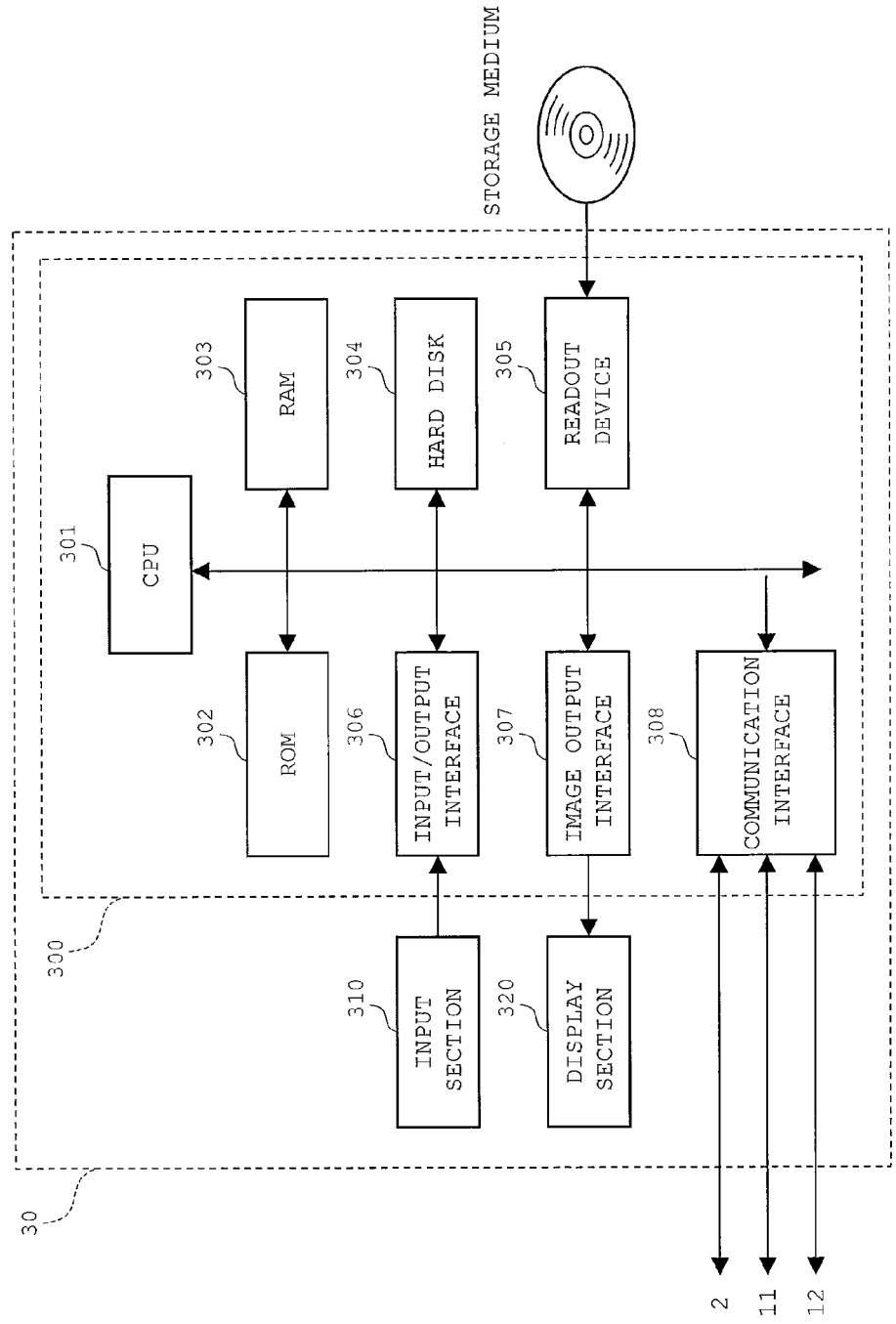
FIG. 4 shows a circuit configuration of an information processing apparatus according to an embodiment.

FIG. 4 shows a circuit configuration of the information processing apparatus 30.

The information processing apparatus 30 is implemented by a personal computer, and includes a body 300, an input section 310, and a display section 320. The body 300 includes a CPU 301, a ROM 302, a RAM 303, a hard disk 304, a readout device 305, an input/output interface 306, an image output interface 307, and a communication interface 308.

The CPU 301 executes computer programs stored in the ROM 302 and computer programs loaded onto the RAM 303. The RAM 303 is used for reading out computer programs stored in the ROM 302 and the hard disk 304. The RAM 303 is also used as a work area for the CPU 301 when the CPU 301 executes these computer programs.

Various computer programs, such as an operating system and application programs, to be executed by the CPU 301, and data used for execution of such computer programs are installed in the hard disk 304. That is, a program for inquiring of the host computer 2 about orders based on later-described order inquiries transmitted from the first measurement apparatus 11 and the second measurement apparatus 12, a program for transmitting orders that have been transmitted from the host computer 2, to the first measurement apparatus 11 and the second measurement apparatus 12, and the like are installed in the hard disk 304. Moreover, a program for causing the display section 320 to perform display and the like based on an analysis result transmitted from the first measurement apparatus 11, a program for analyzing a measurement result transmitted from the second measurement apparatus 12 and for causing the display section 320 to perform display and the like based on the analysis result, and the like are installed in the hard disk 304.

The readout device 305 is implemented by a CD drive, a DVD drive, or the like, and can read out computer programs and data stored in a storage medium. The input section 310 implemented by a mouse and a keyboard is connected to the input/output interface 306. By the user using the input section 310, data is inputted to the information processing apparatus 30. The image output interface 307 is connected to the display section 320 implemented by a display and the like, and outputs video signals corresponding to image data to the display section 320. The display section 320 displays an image based on the inputted video signals. Further, the communication interface 308 allows data transmission/reception between the first measurement apparatus 11, the second measurement apparatus 12, and the host computer 2.

FIG. 5A is a flow chart showing a measurement process performed by the first measurement apparatus 11.

Upon the bar code reader 116 reading out bar code information from the bar code label affixed to a sample container 51 (S101: YES), the CPU 111a of the first measurement apparatus 11 inquires of the information processing apparatus 30 about an order for the sample specified by the bar code information (S102). On the other hand, when bar code information has not been read out (S101: NO), the process is advanced to S108.

Next, the CPU 111a causes the process to wait until receiving the order from the information processing apparatus 30 (S103). Upon receiving the order from the information processing apparatus 30 (S103: YES), the CPU 111a determines, with respect to the sample specified by the bar code information read out in S101, whether it is necessary to perform measurement in the first measurement apparatus 11 (S104). It should be noted that the order includes the type of measurement to be performed by the first measurement apparatus 11, and information of whether measurement is necessary or not. The determination in S104 is performed based on the content of the received order.

When the CPU 111a has determined that it is necessary to perform measurement in the first measurement apparatus 11 (S104: YES), measurement is performed in the first measurement apparatus 11 (S105). That is, the CPU 111a causes the pushing-out mechanism 24 to move the sample rack 50, thereby locating, at the first supply position 26a, the sample container 51 containing the sample for which it has been determined that it is necessary to perform measurement in S104. Then, the CPU 111a causes the nozzle of the first measurement apparatus 11 to aspirate the sample from the sample container 51, and measurement is performed in the first measurement apparatus 11. Subsequently, the CPU 111a analyzes a measurement result of the sample (S106), and transmits the analysis result to the information processing apparatus 30 (S107). On the other hand, when the CPU 111a has determined that it is not necessary to perform measurement in the first measurement apparatus 11 (S104: NO), measurement is not performed for this sample, and the process is advanced to S108.

In this manner, the processes of S101 to S107 are repeatedly performed until the first measurement apparatus 11 is shut down (S108: YES).

FIG. 5B is a flow chart showing a transport process performed by the first measurement apparatus 11. It should be noted that the transport process below is a transport process performed when the sample rack 50 is transported such that a holder of a sample rack 50 located at the first supply position 26a is moved leftward (X-axis positive direction) by the interval between holders.

The CPU 111a of the first measurement apparatus 11 determines whether a measuring operation for the sample in the sample container 51 located at the first supply position 26a has been completed in the first measurement apparatus 11 (S111).

That is, with respect to the sample in the sample container 51 located at the first supply position 26a, in the case where it has been determined that it is necessary to perform measurement in S104 in FIG. 5A and aspiration has been completed in S105, or in the case where it has been determined that it is not necessary to perform measurement in S104, the CPU 111a determines, in S111 in FIG. 5B, that the measuring operation has been completed. Further, also in the case where no sample container 51 is held in the holder of the sample rack 50 located at the first supply position 26a, it is determined as YES in S111.

When it has been determined that the measuring operation in the first measurement apparatus 11 has been completed (S111: YES), the CPU 111a causes the process to wait until a command most recently received from the second measurement apparatus 12 indicates that transportation is allowed (S112). The command transmitted from the second measurement apparatus 12 will be described later with reference to FIG. 6. On the other hand, when it has been determined that the measuring operation has not been completed in the first measurement apparatus 11 (S111: NO), the process is advanced to S116.

When it has been determined that the command most recently received from the second measurement apparatus 12 indicates that transportation is allowed (S112: YES), the CPU 111a drives the pushing-out mechanism 24, whereby the sample rack 50 is transported leftward (X-axis positive direction) by the interval between holders. Accordingly, the holder of the sample rack 50 located at the first supply position 26a is moved leftward (X-axis positive direction) by the interval between holders.

When the sample container 51 is located at the second supply position 26b by being transported in S113 (S114: YES), the CPU 111a transmits, to the second measurement apparatus 12, an aspiration instruction to aspirate the sample in the sample container 51 (S115). On the other hand, when the sample container 51 is not located at the second supply position 26b by being transported in S113 (S114: NO), the process is advanced to S116.

In this manner, the processes of S111 to S115 are repeatedly performed until the first measurement apparatus 11 is shut down (S116: YES).

FIG. 6 is a flow chart showing a measurement process performed by the second measurement apparatus 12.

Upon receiving the aspiration instruction from the first measurement apparatus 11 (S201: YES), the CPU 121a of the second measurement apparatus 12 writes a command indicating that transportation is not allowed, into a buffer in the storage section 121b of the second measurement apparatus 12 (S202). On the other hand, when not having received the aspiration instruction from the first measurement apparatus 11 (S201: NO), the CPU 121a writes a command indicating that transportation is allowed, into the buffer in the storage section 121b (S209). It should be noted that either one of the command indicating that transportation is allowed and the command indicating that transportation is not allowed is written in the buffer in the storage section 121b.

Next, the CPU 121a inquires of the information processing apparatus 30 about an order for the sample in the sample container 51 located at the second supply position 26b (S203). The CPU 121a causes the process to wait until receiving the order from the information processing apparatus 30 (S204). Upon receiving the order from the information processing apparatus 30 (S204: YES), the CPU 121a determines, with respect to the sample in the sample container 51 located at the second supply position 26b, whether it is necessary to perform measurement in the second measurement apparatus 12 (S205). It should be noted that the order includes the type of measurement to be performed by the second measurement apparatus 12 and information of whether measurement is necessary or not. The determination in S205 is performed based on the content of the received order.

When the CPU 121a has determined that it is necessary to perform measurement in the second measurement apparatus 12 (S205: YES), measurement is performed in the second measurement apparatus 12 (S206). That is, the sample container 51 containing the sample for which it has been determined that measurement is necessary in S205 is subjected to aspiration by the nozzle of the second measurement apparatus 12, and measurement is performed in the second measurement apparatus 12. Subsequently, the CPU 121a transmits the measurement result to the information processing apparatus 30 (S207).

Subsequently, the CPU 121a causes the process to wait until the aspiration operation by the nozzle of the second measurement apparatus 12 is completed for the sample in the sample container 51 located at the second supply position 26b and transportation of the sample rack 50 holding this sample container 51 is allowed (S208). When the aspiration operation for this sample is completed and transportation is allowed (S208: YES), the CPU 121a writes a command indicating that transportation is allowed, into the buffer in the storage section 121b (S209).

Also when it has been determined that it is not necessary to perform measurement in the second measurement apparatus 12 for the sample in the sample container 51 located at the second supply position 26b (S205: NO), the CPU 121a writes a command indicating that transportation is allowed, into the buffer in the storage section 121b (S209).

In this manner, the processes of S201 to S209 are repeatedly performed until the second measurement apparatus 12 is shut down (S210: YES).

Figure 7B:
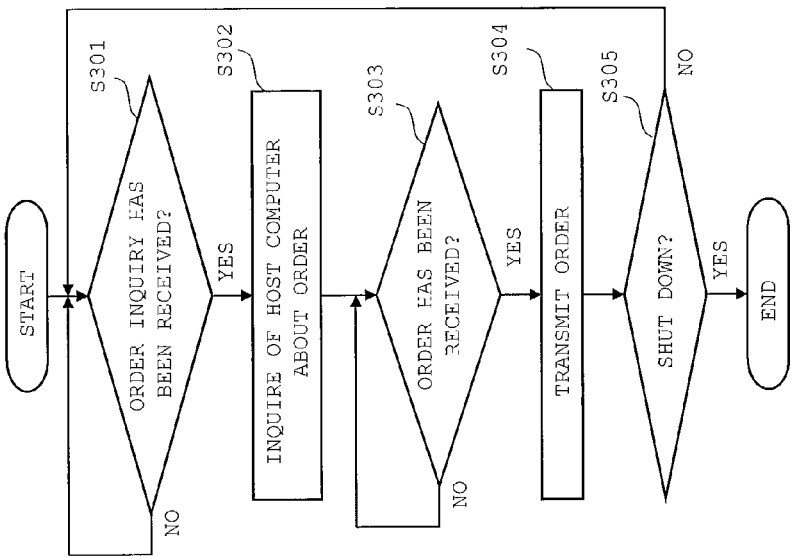
FIGS. 7A and 7B show flow charts respectively showing a command transmitting process performed by the second measurement apparatus and an order process performed by the information processing apparatus according to an embodiment.
Figure 7A:
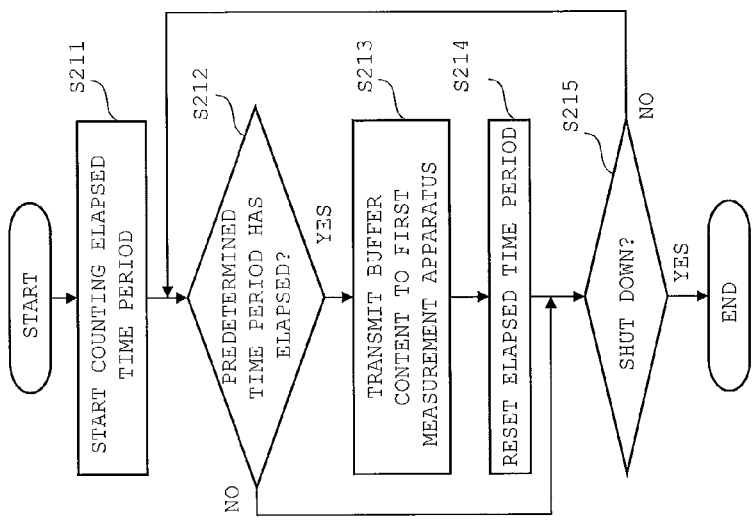

FIG. 7A is a flow chart showing a command transmitting process performed by the second measurement apparatus 12.

First, the CPU 121a of the second measurement apparatus 12 starts counting an elapsed time period (S211). Next, based on the count of the elapsed time period, the CPU 121a determines whether a predetermined time period has elapsed (S212). When the predetermined time period has elapsed (S212: YES), the CPU 121a transmits to the first measurement apparatus 11 the command stored in the storage section 121b of the second measurement apparatus 12 (S213), and resets the elapsed time period (S214).

In this manner, the processes of S212 to S214 are repeatedly performed until the second measurement apparatus 12 is shut down (S215: YES). Accordingly, the command stored in the storage section 121b of the second measurement apparatus 12 is transmitted to the first measurement apparatus 11 every predetermined time period.

FIG. 7B is a flow chart showing an order process performed by the information processing apparatus 30.

The CPU 301 of the information processing apparatus 30 causes the process to wait until receiving an order inquiry from the first measurement apparatus 11 or the second measurement apparatus 12 (S301). Upon receiving an order inquiry (S301: YES), the CPU 301 inquires of the host computer 2 about an order, based on this order inquiry (S302). The host computer 2 determines an order in accordance with the order inquiry.

The CPU 301 causes the process to wait until receiving the order from the host computer 2 (S303) as a result of the order inquiry performed in S302. Upon receiving the order (S303: YES), the CPU 301 transmits the received order to the first measurement apparatus 11 or the second measurement apparatus 12 from which the original order inquiry was received (S304).

In this manner, the processes of S301 to S304 are repeatedly performed until the information processing apparatus 30 is shut down (S305: YES). It should be noted that, when order inquiries are received from the first measurement apparatus 11 and the second measurement apparatus 12, the order processes are performed in parallel.

Figure 8A:
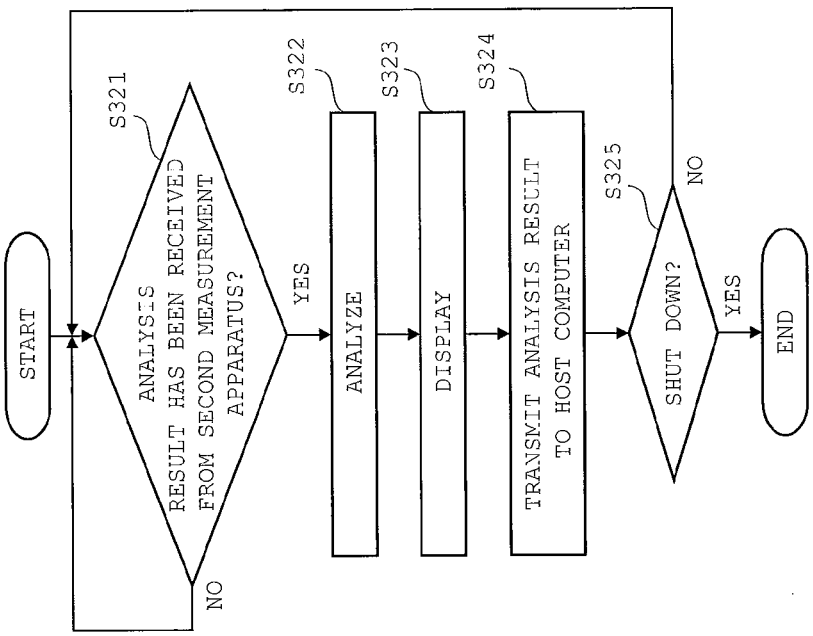
FIGS. 8A and 8B show flow charts respectively showing display processes performed by the information processing apparatus according to an embodiment.
Figure 8B:
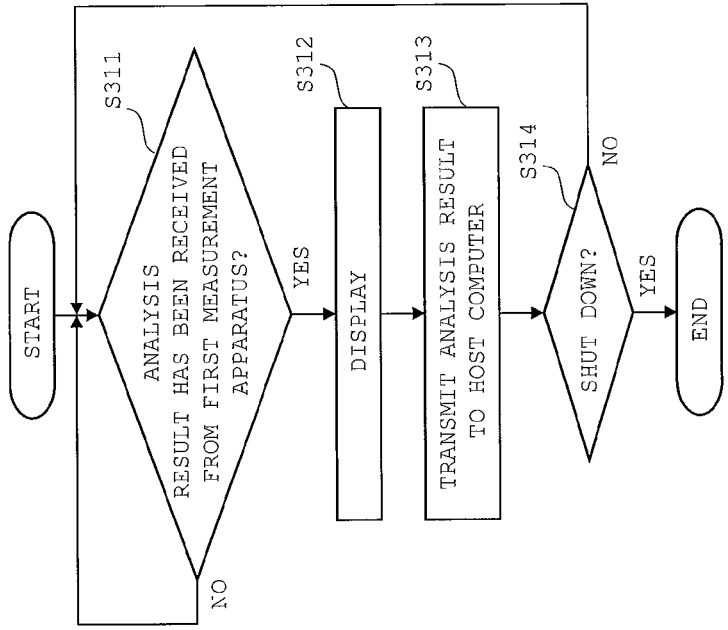

FIG. 8 shows flow charts respectively showing display processes performed by the information processing apparatus 30. FIG. 8A shows a process of displaying an analysis result obtained by the first measurement apparatus 11, and FIG. 8B is a process of displaying an analysis result obtained by the second measurement apparatus 12.

With reference to FIG. 8A, upon receiving an analysis result from the first measurement apparatus 11 (S311: YES), the CPU 301 of the information processing apparatus 30 causes the display section 320 of the information processing apparatus 30 to display the analysis result (S312). Subsequently, the CPU 301 transmits the analysis result to the host computer 2 (S313). Accordingly, analysis results obtained from results of measurements of the sample performed by the first measurement apparatus 11 are accumulated in the host computer 2. When an order inquiry regarding this sample is received from the second measurement apparatus 12, the host computer 2 determines an order in consideration of the analysis results of the sample.

In this manner, the processes of S311 to S313 are repeatedly performed until the information processing apparatus 30 is shut down (S314: YES).

Next, with reference to FIG. 8B, upon receiving a measurement result from the second measurement apparatus 12 (S321: YES), the CPU 301 of the information processing apparatus 30 analyzes the measurement result (S322) and causes the display section 320 of the information processing apparatus 30 to display the analysis result (S323). Subsequently, the CPU 301 transmits the analysis result to the host computer 2 (S324). Accordingly, analysis results obtained from results of measurements of the sample performed by the second measurement apparatus 12 are accumulated in the host computer 2.

In this manner, the processes of S321 to S324 are repeatedly performed until the information processing apparatus 30 is shut down (S325: YES).

As described above, according to the present embodiment, with respect to the sample in the sample container 51 located at the second supply position 26b, from when the second measurement apparatus 12 received an aspiration instruction from the first measurement apparatus 11 until an aspiration operation for the sample is completed and transportation of the sample rack 50 is allowed, or until it is determined that it is not necessary to perform measurement for this sample, a command indicating that transportation is not allowed is transmitted to the first measurement apparatus 11 every predetermined time period. Accordingly, the sample located at the second supply position 26b is not transported unintentionally. Therefore, even if a region for retaining a sample rack 50 is not provided between the first supply position 26a and the second supply position 26b, it is possible to transport the sample rack 50 such that measuring operations can be appropriately performed by the first measurement apparatus 11 and the second measurement apparatus 12. Therefore, it is possible to smoothly transport samples to the two measurement apparatuses while realizing a downsized sample analyzer 1.

Further, according to the present embodiment, the CPU 111a of the first measurement apparatus 11 controls the transporting apparatus 20. Accordingly, there is no need to separately provide a control device for the transporting apparatus 20, and thus, it is possible to further downsize the sample analyzer 1.

Further, according to the present embodiment, the interval between the first supply position 26a and the second supply position 26b is set to be shorter than or equal to the interval between the holders at both ends of the sample rack 50 (the holder at the left end and the holder at the right end). Therefore, it is possible to further downsize the sample analyzer 1. Further, since the time period taken for the transportation from the first supply position 26a to the second supply position 26b is shortened, an aspiration operation by the second measurement apparatus 12 is started in a short time. Accordingly, it is possible to obtain a result of measurement performed by the second measurement apparatus 12 in a short time.

Further, since two sample containers 51 can be concurrently located at the first supply position 26a and the second supply position 26b, it is possible to perform measurements for the two samples in parallel. Therefore, it is possible to obtain a result of measurement performed by the second measurement apparatus 12 in a short time.

An embodiment of the present invention has been described. However, the present invention is not limited to the above embodiment.

For example, in the above embodiment, a subject to be measured is exemplified by urine, but a subject to be measured may be blood. That is, the present invention can also be applied to a sample analyzer which tests blood, and further, the present invention can be applied to a clinical sample analyzer which tests other clinical samples.

Further, in the above embodiment, the interval between the first supply position 26a and the second supply position 26b is set to be shorter than the interval between the holder at the left end of the sample rack 50 and the holder at the right end thereof. However, the present invention is not limited thereto. The interval between the first supply position 26a and the second supply position 26b may be set to be longer than the interval between the holder at the left end of the sample rack 50 and the holder at the right end thereof. In the above embodiment, the transporting apparatus 20 which transports a sample rack 50 which holds ten sample containers 51 has been shown. However, when the present invention is applied to a transporting apparatus which transports a sample rack 50 that holds a smaller number of, e.g., five, sample containers 51, it is possible to prevent the sample processing efficiency from being reduced due to too short an interval between the first supply position 26a and the second supply position 26b.

Further, in the above embodiment, the samples are aspirated from the sample containers 51 located at the first supply position 26a and the second supply position 26b, respectively. However, the present invention is not limited thereto. The sample containers 51 located at the first supply position 26a and the second supply position 26b are taken into the first measurement apparatus 11 and the second measurement apparatus 12, respectively, and the samples may be aspirated from the sample containers 51 in the respective apparatuses.

Further in the above embodiment, the CPU 111a of the first measurement apparatus 11 controls transportation performed by the transporting apparatus 20. However, the present invention is not limited thereto. A controller for controlling transportation performed by the transporting apparatus 20 may be separately provided. Such a controller may be provided in the transporting apparatus 20, for example, or may be incorporated in a transporting apparatus that is separately provided.

Further, in the above embodiment, the CPU 111a is provided in the first measurement apparatus 11 and the CPU 121a is provided in the second measurement apparatus 12. However, the present invention is not limited thereto. These CPUs may be replaced by one CPU. In this case, the replacing one CPU controls transportation performed by the transporting apparatus 20, in accordance with the aspiration status at the second supply position 26b.

Further, in the above embodiment, the CPU 121a of the second measurement apparatus 12 writes a command indicating that transportation is allowed or indicating that transportation is not allowed, into the buffer of the storage section 121b. However, the present invention is not limited thereto. The CPU 121a may write a command indicating a sample aspiration status (for example, information indicating any one of: waiting for sample aspiration; sample being aspirated; sample aspiration completed; and no need for sample aspiration). In this case, the CPU 111a of the first measurement apparatus 11 which has received a command indicating a sample aspiration status controls transportation of the sample rack 50, in accordance with the content of the received command. That is, when the content of the command is "waiting for sample aspiration" or "sample being aspirated", the CPU 111a causes transportation of the sample rack 50 to wait, and when the content of the command is "sample aspiration completed" or "no need for sample aspiration", the CPU 111a causes transportation of the sample rack 50 to be performed, in accordance with the sample measurement status at the first supply position 26a.

Further, in the above embodiment, the CPU 121a of the second measurement apparatus 12 transmits to the first measurement apparatus 11 the command stored in the buffer of the storage section 121b. However, the present invention is not limited thereto. The CPU 111a of the first measurement apparatus 11 may inquire of the second measurement apparatus 12 whether transportation is allowed.

Further, in the above embodiment, the command stored in the buffer of the storage section 121b is transmitted to the first measurement apparatus 11 every predetermined time period. However, the present invention is not limited thereto. The command may be transmitted at a timing at which the status is switched between "transportation is allowed" and "transportation is not allowed".

Further, in the above embodiment, an order is determined by the host computer 2. However, the present invention is not limited thereto. An order may be determined by the CPU 301 of the information processing apparatus 30.

Further, in the above embodiment, the sample analyzer 1 includes the first measurement apparatus 11 which performs urine qualitative tests and the second measurement apparatus 12 which performs urinary sediment tests. However, the present invention is not limited thereto. The sample analyzer 1 may include three or more measurement apparatuses. In the case where the sample analyzer 1 of the above embodiment includes another measurement apparatus, the third measurement apparatus may be, for example, a measurement apparatus that performs urine chemical quantification tests. In this case, the first supply position 26a and the second supply position 26b described above are set also for the second and third measurement apparatuses, as well as for the first and second measurement apparatuses, and similar processes shown in FIG. 5 to FIG. 8 are performed.

In addition to the above, various modifications can be made as appropriate without departing from the scope of the technical idea defined by the claims.

What is claimed is:

1. A sample analyzer which transports and analyzes samples, comprising:
   a first measurement apparatus configured to test samples;
   a second measurement apparatus arranged downstream of the first measurement apparatus in a transport direction, and configured to test at least some of the samples that have been tested by the first measurement apparatus and are found, from test results from the first measurement apparatus, necessary to be further tested;
   a transporting apparatus configured to transport the samples in a rack along a transport path which includes a first supply position at which the samples are tested at the first measurement apparatus, and a second supply position, located downstream of the first supply position, at which the at least some of the samples are tested at the second measurement apparatus, wherein the rack has a line of holders at a regular pitch for holding a predetermined number of the samples, and the first and second supply positions are separated along the transport path at a distance equal to a distance between first and second samples stored in the rack such that the first and second samples are simultaneously positioned, respectively, at the first and second supply positions, and further wherein the first and second measurement apparatuses are operable to conduct their tests in parallel on the first and second samples positioned at the first and second supply positions; and a controller comprising a memory that stores programs for programming the controller, the controller being programmed to coordinate transportation of the rack with progresses of the tests performed by the first measurement apparatus on the first sample positioned at the first supply position and by the second measurement apparatus on the second sample positioned at the second supply position, the controller further programmed to:

keep the rack from being transported until an aspiration is completed from the second sample positioned at the second supply position if an aspiration is completed from the first sample at the first supply position but an aspiration is not completed from the second sample at the second supply position; and after an aspiration is completed from the first sample at the first supply position, transport the rack downstream by one pitch to advance a next sample located in the rack by one pitch upstream of the second sample to the second supply position, without transporting the rack upstream to move the second sample back to the first supply position, when an aspiration becomes completed from the second sample at the second supply position or it is determined that no aspiration is needed at the second supply position.

2. The sample analyzer according to claim 1, wherein the controller is programmed to generate transportability information based on the progress of the test performed by the second measurement apparatus on the second sample positioned at the second supply position, the transportability information indicating whether or not the second sample at the second supply position may be advanced downstream from the second supply position, and transport the rack downstream when the transportability information indicates that the second sample at the second supply position may be advanced downstream from the second supply position.

3. The sample analyzer according to claim 2, wherein when the transportability information indicates that the second sample at the second supply position may not be advanced downstream from the second supply position, the controller is programmed to keep the rack from being transported, until the transportability information switches to indicate that the second sample at the second supply position may be advanced downstream from the second supply position.

4. The sample analyzer according to claim 3, wherein the controller is programmed to switch the transportability information to indicate that the second sample at the second supply position may be advanced downstream from the second supply position when an aspiration becomes completed from the second sample positioned at the second supply position.

5. The sample analyzer according to claim 1, wherein the controller comprises a first processor which controls sample testing performed by the first measurement apparatus and which controls sample transportation performed by the transporting apparatus.

6. The sample analyzer according to claim 5, wherein the controller further comprises a second processor which controls sample testing performed by the second measurement apparatus.

7. The sample analyzer according to claim 6, wherein the first processor and the second processor are connected to establish a data communication between them, the second processor is configured to monitor the progress of the test performed by the second measurement apparatus on the second sample positioned at the second supply position, and the first processor sends an inquiry about the progress of the test on the second sample to the second processor every time a predetermined time elapsed or every time a predefined event occurs.

8. The sample analyzer according to claim 1, wherein the transporting apparatus is a single unit.

9. The sample analyzer according to claim 1, wherein the transport path connecting the first and second supply positions is linear.

10. The sample analyzer according to claim 1, wherein the distance between the first supply position and the second supply position is shorter than or equal to an interval between the holders located at ends of the rack.

11. The sample analyzer according to claim 1, wherein the first measurement apparatus is a urine qualitative measurement apparatus, and the second measurement apparatus is a urinary sediment measurement apparatus.

12. The sample analyzer according to claim 1, wherein the transporting apparatus is configured to transport a sample in a sample container, and at least one of the first and second measurement apparatuses is configured to aspirate the sample in the sample container at the first or second supply position.

13. The sample analyzer according to claim 1, wherein the transporting apparatus is configured to transport a sample in a sample container, and at least one of the first and second measurement apparatuses is configured to take the sample container from the first or second supply position into the at least one of the first and second measurement apparatuses, and then to aspirate the sample in the sample container.

14. The sample analyzer according to claim 1, wherein the transporting apparatus includes:
a first sample storage configured to store one or more unprocessed samples;
a second sample storage configured to store one or more processed samples; and
a connection part that connects the first and second sample storages, the connection part extending along the transport direction.

15. The sample analyzer according to claim 14, wherein the connecting part has a width that allows only one rack to be passed therethrough in a length direction of the rack.

16. A method executed in a sample analyzer that comprises:
a first measurement apparatus configured to test samples;
a second measurement apparatus arranged downstream of the first measurement apparatus in a transport direction, and configured to test at least some of the samples that have been tested by the first measurement apparatus and are found, from test results from the first measurement apparatus, necessary to be further tested;
a transporting apparatus configured to transport the samples in a rack along a transport path which includes a first supply position at which the samples are tested at the first measurement apparatus, and a second supply position, located downstream of the first supply position, at which the at least some of the samples are tested at the second measurement apparatus, wherein the rack has a line of holders at a regular pitch for holding a predetermined number of the samples, and the first and second supply positions are separated along the transport path at a distance equal to a distance between first and second samples stored in the rack such that the first and second samples are simultaneously positioned, respectively, at the first and second supply positions, and further wherein the first and second measurement apparatuses are operable to conduct their tests in parallel on the first and second samples positioned at the first and second supply positions, the method comprising:

controlling the transporting apparatus to transport the rack along transport path to advance the first sample to the first supply position for testing at the first measurement apparatus and to advance the second sample to the second supply position for testing at the second measurement apparatus;

controlling the first and second measurement apparatus to perform the tests on the first and second samples at the first and second supply positions;

keeping the rack from being transported until an aspiration is completed from the second sample positioned at the second supply position if an aspiration is completed from the first sample at the first supply position but an aspiration is not completed from the second sample at the second supply position; and after an aspiration is completed from the first sample at the first supply position, transporting the rack downstream by one pitch to advance a next sample located in the rack by one pitch upstream of the second sample to the second supply position, without transporting the rack upstream to move the second sample back to the first supply position, when an aspiration becomes completed from the second sample at the second supply position or it is determined that no aspiration is needed at the second supply position.

* * * * *